(12) United States Patent
Kellomaki et al.

(10) Patent No.: US 7,848,561 B2
(45) Date of Patent: Dec. 7, 2010

(54) DETERMINING CAPABILITY OF AN ON-LINE SENSOR

(75) Inventors: Markku M. Kellomaki, Kuopio (FI); Antti N. Paavola, Tampere (FI)

(73) Assignee: Honeywell International Inc., Morristown, NJ (US)

( * ) Notice: Subject to any disclaimer, the term of this patent is extended or adjusted under 35 U.S.C. 154(b) by 976 days.

(21) Appl. No.: 11/323,617

(22) Filed: Dec. 30, 2005

(65) Prior Publication Data

US 2007/0154080 A1 Jul. 5, 2007

(51) Int. Cl.
- G06K 9/00 (2006.01)
- G06K 9/46 (2006.01)
- G06K 9/66 (2006.01)
- H04N 17/00 (2006.01)
- G01N 21/84 (2006.01)

(52) U.S. Cl. ............... 382/141; 382/190; 382/204; 348/180; 348/187; 356/429

(58) Field of Classification Search ............. 382/108, 382/111, 141, 149, 190, 204, 212, 214, 217; 348/177, 180, 187; 356/429; 324/527, 530
See application file for complete search history.

(56) References Cited

U.S. PATENT DOCUMENTS

| | | | |
|---|---|---|---|
| 4,324,459 A | | 4/1982 | Gerharz |
| 4,377,338 A | | 3/1983 | Ernst |
| 4,628,342 A | | 12/1986 | Desmons et al. |
| 5,317,646 A | | 5/1994 | Sang, Jr. et al. |
| 5,383,018 A | | 1/1995 | Sadjadi |
| 5,406,070 A | | 4/1995 | Edgar et al. |
| 5,453,840 A | * | 9/1995 | Parker et al. ............... 356/400 |
| 5,764,386 A | * | 6/1998 | Robinson ..................... 358/504 |
| 5,774,519 A | | 6/1998 | Lindstrom et al. |
| 5,821,993 A | * | 10/1998 | Robinson ..................... 348/187 |
| 5,884,118 A | * | 3/1999 | Mestha et al. ................. 399/15 |
| 6,063,531 A | * | 5/2000 | Singh et al. ................... 430/30 |
| 6,222,934 B1 | | 4/2001 | Tsai |
| 6,437,823 B1 | | 8/2002 | Zhang |
| 6,488,353 B1 | | 12/2002 | Itoyama et al. |
| 6,654,493 B1 | * | 11/2003 | Hilliard et al. ............... 382/167 |
| 6,768,958 B2 | * | 7/2004 | Ivanovic et al. ............... 702/94 |
| 6,816,187 B1 | * | 11/2004 | Iwai et al. ..................... 348/187 |
| 6,819,789 B1 | * | 11/2004 | Kantor et al. ................. 382/151 |
| 6,956,203 B2 | * | 10/2005 | Staton et al. ............. 250/252.1 |

(Continued)

OTHER PUBLICATIONS

Reder, Alan. "Remote Diagnosis for Laboratory Instruments." IVD Technology. IVD Technology, Jan 2001. Web. Aug. 10, 2010. <http://www.ivdtechnology.com/article/remote-diagnostics-laboratory-instruments>.*

(Continued)

*Primary Examiner*—Matthew C Bella
*Assistant Examiner*—Michael A Newman
(74) *Attorney, Agent, or Firm*—Munck Carter, LLP (57) ABSTRACT

Devices, systems and methods for determining capabilities of an on-line sensor are disclosed. The exemplary method may comprise the following acts. The method may generate an image of a sample texture with known characteristics. The method may transfer the image to an on-line sensor. The method may also analyze data generated by the on-line sensor to determine measured characteristics. The method may compare the measured characteristics to the known characteristics.

21 Claims, 6 Drawing Sheets

U.S. PATENT DOCUMENTS

| | | | |
|---|---|---|---|
| 6,985,251 B2* | 1/2006 | Okahashi et al. | 358/1.3 |
| 7,023,473 B2* | 4/2006 | Iwai et al. | 348/187 |
| 7,085,408 B1* | 8/2006 | Chung-Chi Jim | 382/149 |
| 2002/0041383 A1* | 4/2002 | Lewis et al. | 358/1.9 |
| 2002/0198673 A1* | 12/2002 | Koeberle et al. | 702/108 |
| 2003/0210431 A1* | 11/2003 | Rylander | 358/3.06 |
| 2005/0083531 A1* | 4/2005 | Millerd et al. | 356/450 |
| 2005/0100205 A1* | 5/2005 | Shishido et al. | 382/145 |
| 2005/0146722 A1* | 7/2005 | Torfs et al. | 356/402 |
| 2005/0190961 A1* | 9/2005 | Beaty et al. | 382/150 |
| 2008/0019611 A1* | 1/2008 | Larkin et al. | 382/287 |

OTHER PUBLICATIONS

Sjodahl et al., Electronic Speckle Photography: Analysis of an Algorithm Giving the Displacement with Subpixel Accuracy, Applied Optics, vol. 32, No. 13, 1993, pp. 2278-2284.

* cited by examiner

DETERMINING CAPABILITY OF AN ON-LINE SENSOR

FIELD OF THE INVENTION

The present invention relates generally to determining capabilities of a sensor, and more particularly to determining quality characteristics of an on-line sensor in a manufacturing process.

BACKGROUND OF THE INVENTION

Manufacturers may need to monitor and control the product quality using on-line sensors during processing of the product. An on-line sensor may be used to determine characteristics of the product texture during the processing of the product. The on-line sensor may receive a beam of light reflected off the surface of the product or transmitted through the product. The on-line sensor may then analyze the reflected or transmitted light and the original beam of light to determine qualities of the product texture. The product may be, for example, paper or a sheet of material.

The manufacturing environment may produce conditions that may affect the accuracy of the on-line sensor. For example, vibrations of components used in the processing of the product, temperature variations, and/or dust produced during processing of the product may reduce the accuracy of the on-line sensor.

In order to verify the accuracy of on-line sensors, a sample of the product may be measured in a laboratory. In a controlled laboratory environment, laboratory sensors may be used to attempt to provide a more accurate measurement of the sample. The sample is also tested using the on-line sensor. The results of the laboratory sensor are compared with the on-line sensor to identify the accuracy and/or capabilities of the on-line sensor.

However, an undesirable situation may result when the on-line sensor has higher capability than the laboratory sensor, which then may lead to poor correlation between the sensors. The results may then be interpreted as the fault of the on-line sensor. Accordingly, an efficient and effective device, method, and system are needed for providing more accurate comparisons between the true qualities of a sample texture and measured qualities of an on-line sensor. In addition, the device, system and method may need to provide a more accurate comparison between the true qualities of a sample texture, laboratory measured qualities of the sample texture and the measured qualities by an on-line sensor of the sample texture.

SUMMARY OF THE INVENTION

It is, therefore, an object of the present invention to provide devices, systems, and methods for determining capabilities of an on-line sensor. According to an exemplary embodiment of the present invention, the method may generate an image of a sample texture with known characteristics. The exemplary method may transfer the image to an on-line sensor. The exemplary method may analyze data generated by the on-line sensor to determine measured characteristics and compare the measured characteristics to the known characteristics.

According to an exemplary embodiment of the present invention, the device may incorporate the following embodiments. In one embodiment, generating an image of a sample texture may involve a computer algorithm generating a two-dimensional matrix of a disordered medium. The act of generating an image of a sample texture may also involve generating a two-dimensional matrix of a disordered medium from an image of a known textured surface. In another embodiment, transferring the image may involve printing an image copy and presenting the image copy to the on-line sensor. In an additional embodiment, transferring the image may involve displaying an image copy and presenting the displayed image copy to the on-line sensor. In yet another embodiment, transferring the image may involve displaying an image copy and reflecting the displayed image copy onto the on-line sensor. In another embodiment, the exemplary method may further involve transferring the image to a laboratory sensor; analyzing data generated by the laboratory sensor to determine measured characteristics; and comparing the known characteristics to the measured characteristics of the on-line sensor and to the measured characteristics of the laboratory sensor. In another embodiment, comparing the known characteristics may involve generating a mathematical formula of a cross-correlation between the measured characteristics and the known characteristics.

BRIEF DESCRIPTION OF THE DRAWINGS

The above and other objectives and advantages of the present invention will be apparent upon consideration of the following detailed description, taken in conjunction with the accompanying drawings, in which like reference numbers refer to like parts throughout, and in which.

DETAILED DESCRIPTION OF THE INVENTION

The present invention provides a device, system, and method to monitor and control the quality of on-line sensors measurements. An on-line sensor may be used to determine characteristics of a product's texture during the processing of the product. The product may be, for example, paper, woven fabric, or a minor periodic textures in otherwise disordered media, for example, a wire mark in paper. The on-line sensor may utilize a photo detector to receive a beam of light reflected off the product or transmitted through the product. The photo detector converts the received light into an electrical signal. The electrical signal is analyzed to determine characteristics of the texture.

The present invention generates a sample texture with known characteristics. The sample texture may be generated by a computer producing a two-dimensional matrix with mathematical algorithms. The sample texture may be printed on a medium and placed in an inspection area of the on-line sensor or the sample texture may be reflected onto the on-line sensor. The on-line sensor determines the characteristics of the sample texture. The characteristics generated by the on-line sensor are compared to the known characteristics of the sample texture to determine the quality of the on-line sensor.

The computer-generated sample texture may provide specific properties and reference points for the on-line sensor measurement to be assessed. The capability of the on-line sensor device can be quantified without the disadvantages related to material samples supplied through the production process. The computer-generated sample texture may also provide a calibration between differently designed measurement devices. For example, measurement sensors designed and built by different manufacturers may be analyzed with respect to one another. In the case of low correlation between the measurement sensors, the more accurate one may objectively be identified. In addition, the base calibration (factory calibration) and inter-sensor calibration can be made more accurate using the invention.

Figure 1:
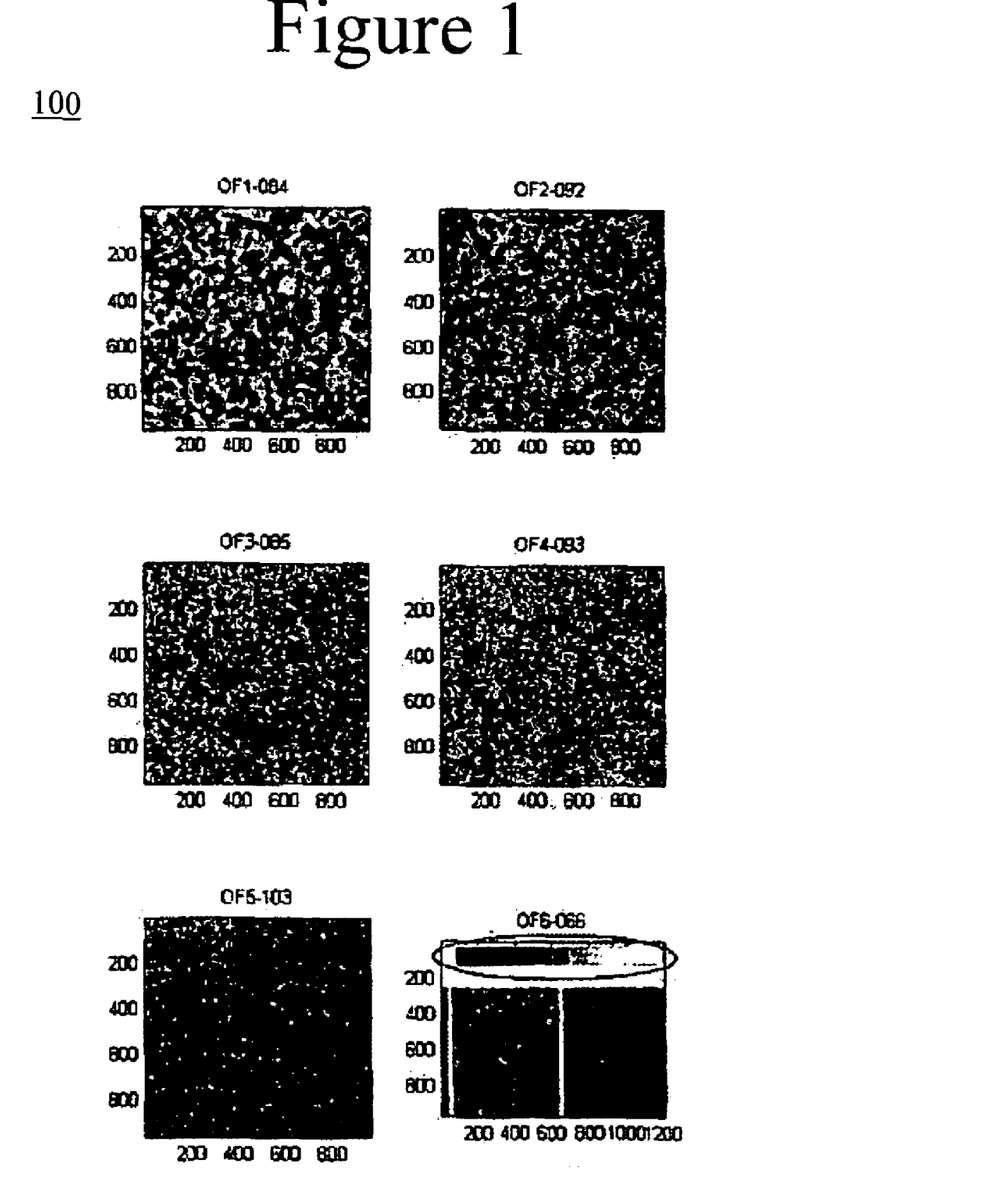
FIG. 1 illustrates images of computer simulated sample textures printed on a transparent medium.

Referring to FIG. 1, five images OF1-OF5 of computer simulated sample textures and a sample including a grayscale step target OF6 are shown. The five images OF1-OF5 of the sample texture are printed on a transparent medium with an inkjet printer using the methods and devices described herein.

Figure 2:
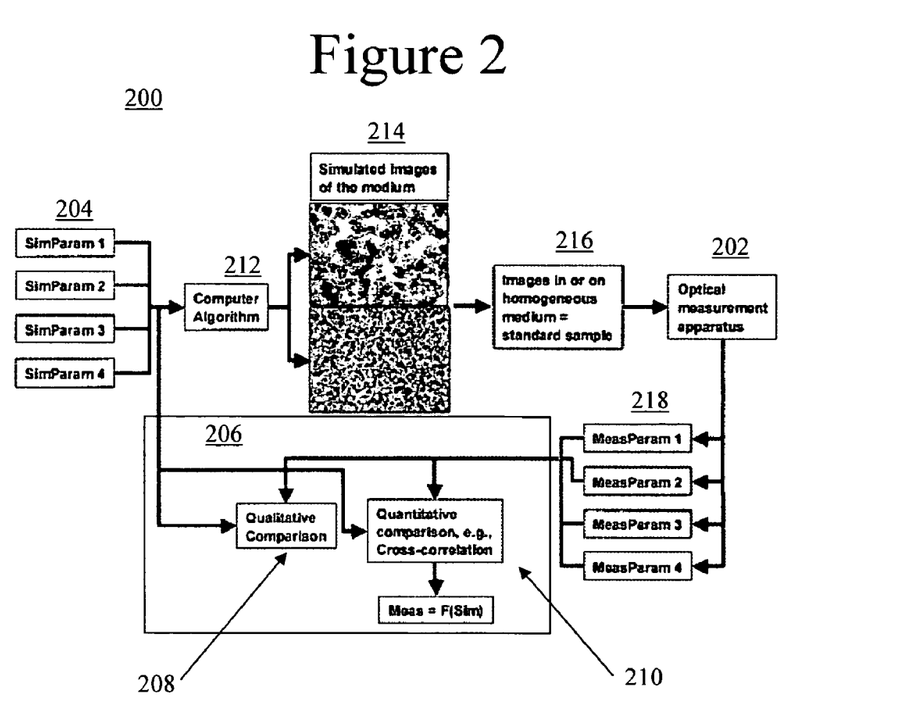
FIG. 2 is a generalized schematic of a sampling device used to implement a first exemplary sampling embodiment of the present invention.

Referring to FIG. 2, a sampling device 200 according to a first exemplary sampling embodiment is used to evaluate a sensor. The sampling device 200 may be used to determine the capabilities of an on-line sensor 202. The user of the sampling device 200 may select and set one or more simulation parameters 204 for a simulated sample texture. The generation of the texture is controlled using the parameters in order to achieve desired properties, e.g., mimicking real-life samples in some manufacturing process operating point. The simulation parameters 204 may be properties of a typical texture examined by sensors 202. The simulation parameters 204 are fed into an analyzing device 206. The analyzing device 206 may feed the simulation parameters 204 into a qualitative comparator 208 and a quantitative comparator 210. The analysis performed by the qualitative comparator 208 and the quantitative comparator 210 is discussed later herein. The one or more simulation parameters 204 are also fed into a computer algorithm 212.

The computer algorithm 212 may generate a two-dimensional array with statistical properties typical of a medium being analyzed based on the simulation parameters 204. The computer algorithm 212 may be a statistical simulation building the image from basic constituents of the medium, for example, simulation parameters 204 of the fibers or other product components. The computer algorithm 212 may also be based on mathematical formulas, for example, fractals that produce statistical properties similar to the disordered properties typical of the medium. The computer algorithm 212 may also use a combination of both simulation and mathematical formulas. The two-dimensional array may provide a non-homogeneous medium with or without repeatable structures.

An image 214 of the sample texture may be generated from the two-dimensional array. A printing device 216 may be used to produce the image 214 on or into a homogeneous medium. The homogeneous medium may be, for example, but not limited to, film, transparency, semi-opaque or non-opaque printing medium. In another example, a non-homogeneous medium may be used. According to this example, the simulation parameters 204 may be designed to take into account the non-homogeneous structure of the medium. The printing device 216 used to print may be a variety of devices known to an individual skilled in the art. In yet another example, the printing device 216 may be etched or machined on to a medium. The image 214 would provide a surface topography of the sample texture, for example, the fiber orientation of a sample. The printing device 216 may be selected based on the medium selected to display the image 214.

The image 214 on the medium is placed in the detection area of the on-line sensor 202. The on-line sensor 202 scans the image 214 displayed on the homogeneous medium. The on-line sensor 202 may scan the sample using a variety of radiation sources, for example, light, x-ray, and electron beam. The conditions used to scan the image 214 on the homogeneous medium may be designed to be similar to the actual conditions seen during normal operation of the on-line sensor 202. For example, the image 214 may be displayed in front of the on-line sensor 202 using the same conveying device used during normal operation.

The on-line sensor 202 or a component of the on-line sensor may separate the image 214 viewed by the on-line sensor 202 down into measured parameters 218. These measured parameters 218, may be, for example, but not limited to the reflected or transmitted illumination detected by the on-line sensor 202 or the variability of illumination detected by the on-line sensor 202. The measured parameters 218 are fed into the analyzing device 206. The analyzing device 206 may feed the measured parameters into the qualitative comparator 208 and the quantitative comparator 210. The qualitative comparator 208 and the quantitative comparator 210 compare the simulation parameters 204 to the measured parameters 218. The analyzing device 206 may provide an accurate comparison of the on-line sensor 202 to other sensors. Additional manipulation of the parameters 204, 218 may be provided to produce a better understanding of the accuracy of the on-line sensor 202. For example, the quantitative device 210 may be used to provide a cross-correlation between the simulation parameters 204 and the measured parameters 218. In addition, mathematical formulas may be generated to depict and/or predict the error of the on-line sensor 202.

The systems and methods used by the computer algorithms 212 and analyzing device 206 on the simulation parameters 204 and measured parameters 218 may be incorporated in software used with a computer or other suitable operating device. Architecturally in terms of hardware, the simulation parameters 204, computer algorithms 212, measured parameters 218, and analyzing device 206 may utilize a processor, memory, and one or more input and output interface devices. The various interface devices may have additional elements, which are omitted for simplicity, such as controllers, buffers (caches), drivers, repeaters, and receivers, to enable communications. As previously discussed the image 214 produced by the computer algorithm 212 may be supplied to a printing device 216 coupled to an interface device. The software may also provide a Graphic User Interface (GUI) to allow the administrator or user to enter, edit, view and/or store the image 214 as well as simulation parameters 204. Similarly, the analyzing device 206 may also use a GUI to allow the administrator to analyze, edit, view and/or store data associated with the comparison of the simulation parameters 204 and measured parameters 218.

Figure 3:
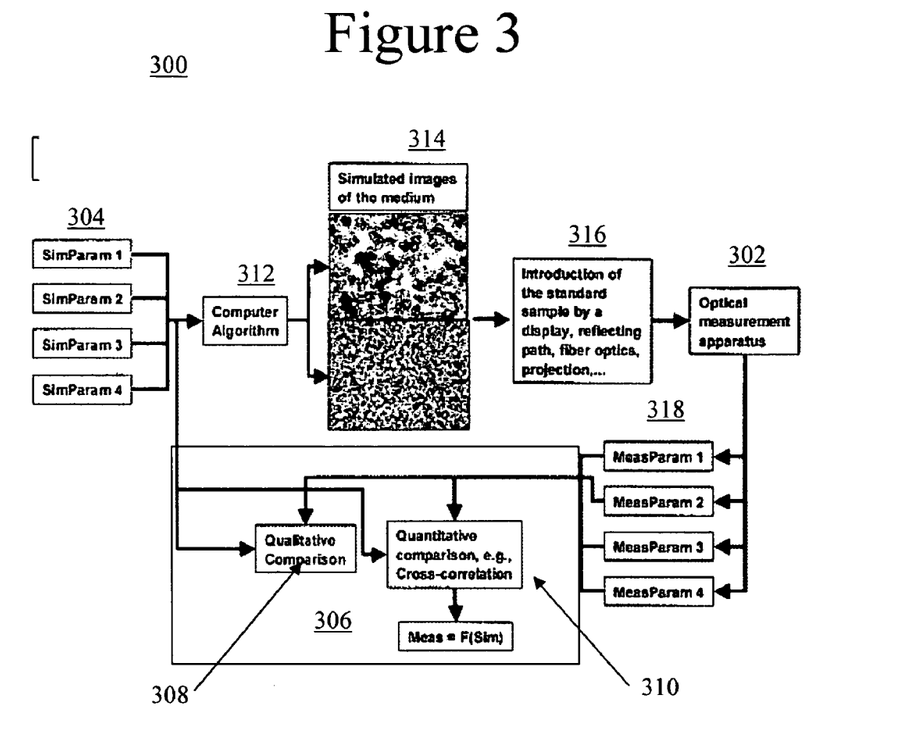
FIG. 3 is a generalized schematic of a sampling device used to implement a second exemplary sampling embodiment of the present invention.

Referring to FIG. 3, a sampling device 300 according to a second exemplary sampling embodiment is used to evaluate a sensor. The sampling device 300 may be used to determine the capabilities of an on-line sensor 302. The sampling device 300 generates one or more simulation parameters 304 of a simulated sample texture. The simulated parameters 304 may be properties of a typical texture examined by sensors 302. The simulation parameters 304 are fed into an analyzing device 306. The analyzing device 306 may feed the simulation parameters 304 into a qualitative comparator 308 and a quantitative comparator 310. The analysis performed by the qualitative comparator 308 and the quantitative comparator 310 is discussed later herein. The one or more simulation parameters 304 are also fed into a computer algorithm 312.

The computer algorithm 312 may generate an image 314 similar to that discussed with regard to the first exemplary sampling embodiment. A display device 316 may be used to produce the image 314 on or into the on-line sensor 302. Similarly to the example discussed with regard to the first exemplary sampling embodiment, the simulation parameters 304 may be designed to take into account characteristics of the display device 316. The displaying device 316 used to display may be a variety of devices known to an individual skilled in the art. The device may be selected based on the on-line sensor 302 and characteristics of the image 314. The display device 316 may use components and methods to display the image 314 in or onto the on-line sensor 302, for example, optical reflecting components, fiber optics, projection, and holograms.

The on-line sensor 302 scans the image 314 displayed. The on-line sensor 302 or a component of the on-line sensor may separate the image 314 viewed by the on-line sensor 302 into measured parameters 318. The measured parameters 318 are fed into the analyzing device 306. The analyzing device 306 may feed the measured parameters into the qualitative comparator 308 and the quantitative comparator 310. The qualitative comparator 308 and the quantitative comparator 310 compare the simulation parameters 304 to the measured parameters 318. The analyzing device 306 may provide an accurate comparison of the on-line sensor 302 to other sensors similar to the first exemplary sampling embodiment.

Figure 4:
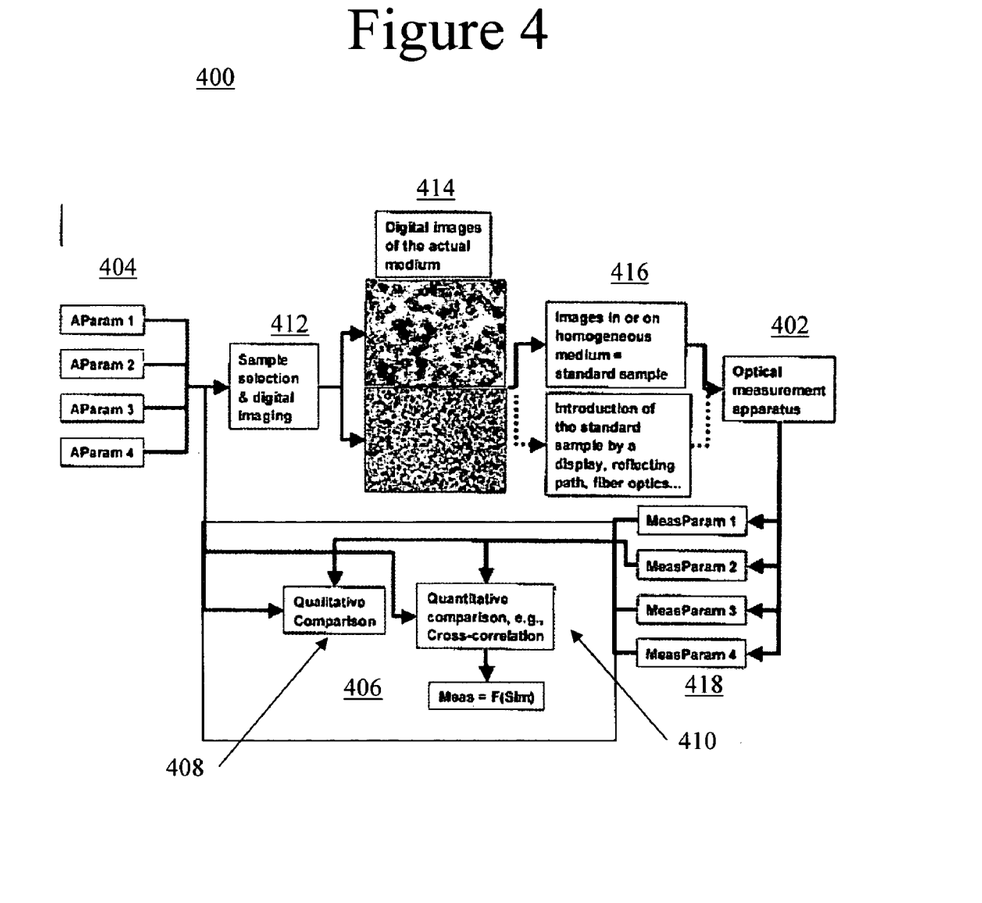
FIG. 4 is a generalized schematic of a sampling device used to implement a third exemplary sampling embodiment of the present invention.

Referring to FIG. 4, a sampling device 400 according to a third exemplary sampling embodiment is used to evaluate a sensor. The sampling device 400 may be used to determine the capabilities of an on-line sensor 402. The sampling device 400 generates one or more assessed parameters 404 from an image of a sample texture by scientific instrument, visual inspection, or a combination of both. The assessed parameters 404 may be determined by scanning a known sample using a variety of radiation sources, for example, light, x-ray, and electron beam. The assessed parameters 404 may provide properties of a typical texture examined by sensors 402. The texture samples are selected so that their assessment parameters can be determined by other known accurate methods, for example, visual inspection.

The assessed parameters 404 are fed into an analyzing device 406. The analyzing device 406 may feed the assessed parameters 404 into a qualitative comparator 408 and a quantitative comparator 410. The analysis performed by the qualitative comparator 408 and the quantitative comparator 410 is discussed later herein. The one or more of the assessed parameters 404 are also fed into a computer algorithm 412.

The computer algorithm 412 may generate an image 414 similar to that discussed with regard to the first exemplary sampling embodiment. The process of "generating" samples in this embodiment duplicates the textures of the selected samples electronically. A printing device or display device 416 may be used to produce the image 414 on or into the on-line sensor 402, as previously discussed with regard to the first and second exemplary sampling embodiments.

The on-line sensor 402 scans and separates the image 414 viewed by the on-line sensor 402 into measured parameters 418. The measured parameters 418 are fed into the analyzing device 406. The analyzing device 406 may feed the measured parameters into the qualitative comparator 408 and the quantitative comparator 410. The qualitative comparator 408 and the quantitative comparator 410 compare the assessed parameters 404 to the measured parameters 418. The analyzing device 406 may provide an accurate comparison of the on-line sensor 402 to other sensors similar to the first exemplary sampling embodiment.

Figure 5:
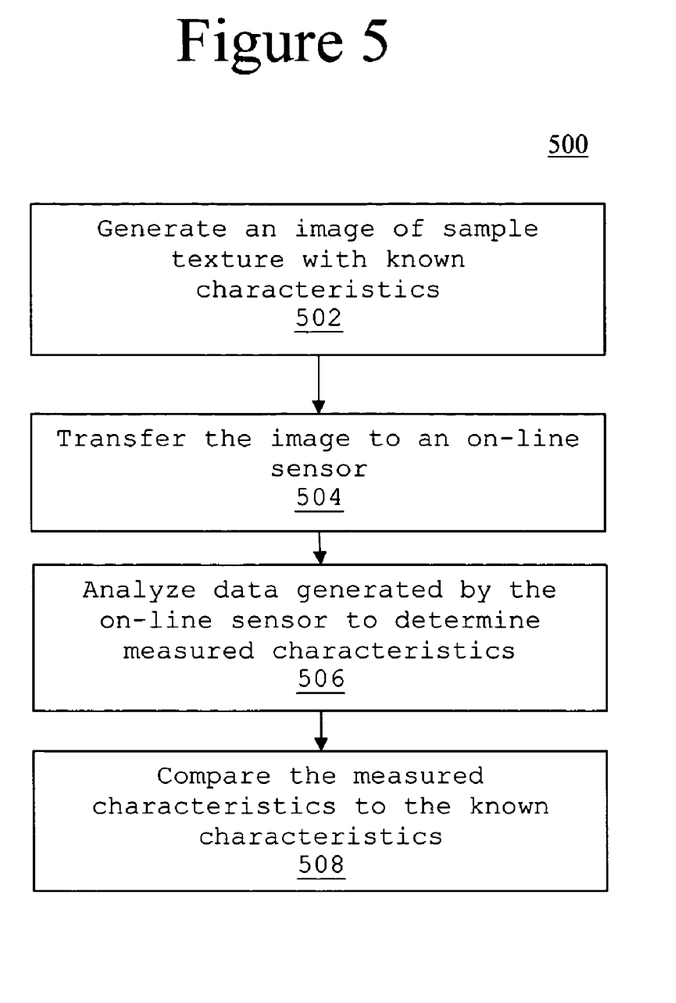
FIG. 5 is a flow chart illustrating a first exemplary sampling method embodiment of the present invention.

Referring to FIG. 5, a flow chart illustrates a first exemplary sampling method 500 embodiment of the present invention. The sampling process generates an image of a sample texture with known characteristics (block 502). As previously discussed, the image may be produced using simulation parameters 204, 304 or assessed parameters 404. The image is transferred to an on-line sensor (block 504). This may be accomplished with a printing device 216 or a display device 316. The on-line sensor produces measured parameters of the image (block 506). Analyzing device 206, 306, 406 compares the measured characteristics to the known characteristics (block 508). An accurate comparison of the on-line sensor 202, 302, 402 to other sensors may be provided as discussed with regard to the first exemplary sampling embodiment.

Figure 6:
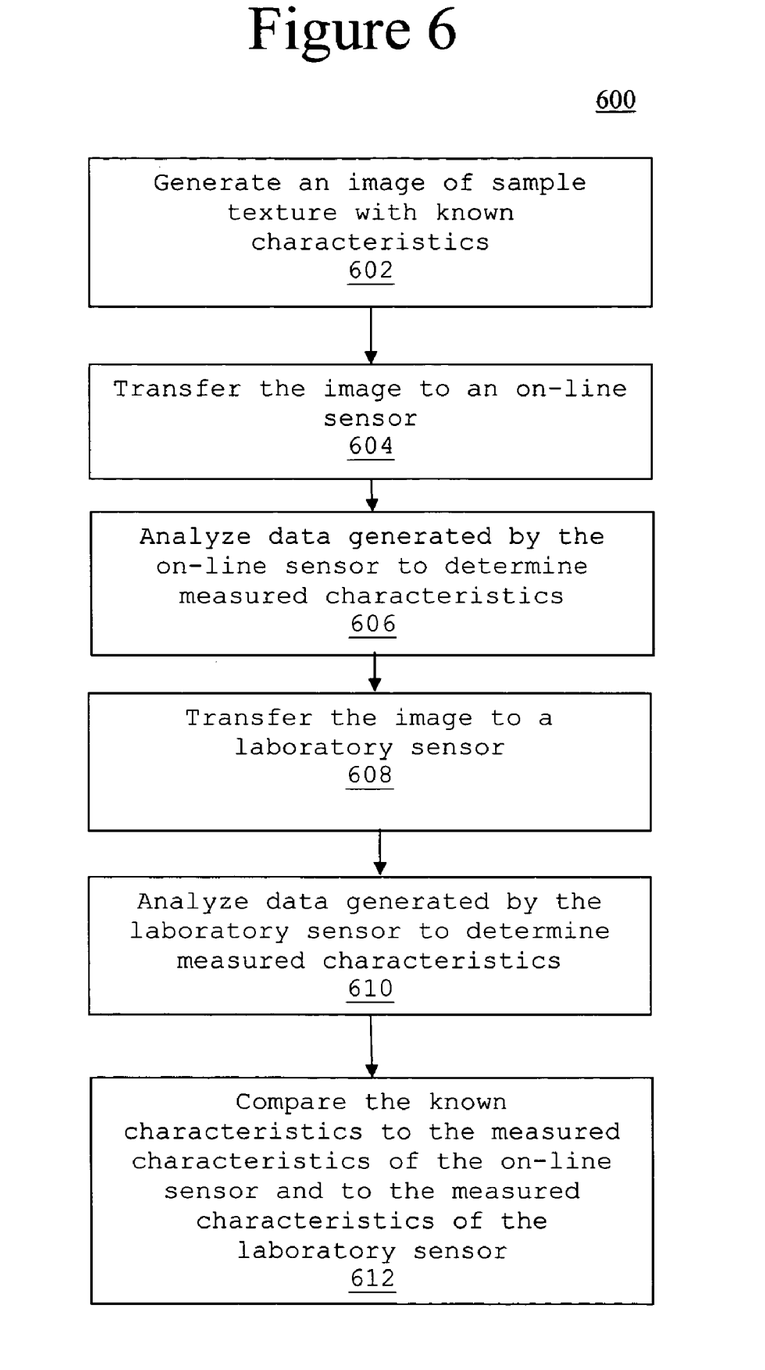
FIG. 6 is a flow chart illustrating a second exemplary sampling method embodiment of the present invention.

Referring to FIG. 6, a flow chart illustrates a second exemplary sampling method 600 embodiment of the present invention. The sampling process generates an image of a sample texture with known characteristics (block 602). As previously discussed, the image may be produced using simulation parameters 204, 304 or assessed parameters 404. The image is transferred to an on-line sensor (block 604). This may be accomplished with a printing device 216 or a display device 316. The on-line sensor produces measured parameters of the image (block 606). The image is transferred to a laboratory sensor (block 608). This may be accomplished with a printing device 216 or a display device 316. The laboratory sensor produces measured parameters of the image (block 610). An analyzing device 206 compares the known characteristics to the measured characteristics of the on-line sensor and to the measured characteristics of the laboratory sensor (block 612). The second exemplary sampling method may be used to provide an accurate comparison between a laboratory sensor and an on-line sensor.

It will be understood that the foregoing is only illustrative of the principles of the invention and that various modifications can be made by those skilled in the art without departing from the scope and spirit of the invention. For example, the various embodiments described herein may comply with various known standards, for example, the Technical Association of the Pulp and Paper Industry (TAPPI) standards as well as other known industry and government standards. The sample texture may not be limited to a web of paper.

Accordingly, such embodiments will be recognized as within the scope of the present invention. Persons skilled in the art will also appreciate that the present invention can be practiced by other than the described embodiments, which are presented for purposes of illustration rather than of limitation and that the present invention is limited only by the claims that follow.

What is claimed is:

1. A method for determining one or more capabilities of an on-line sensor comprising:

receiving, at the on-line sensor, light that has interacted with a product being produced by a production process;

converting the received light into electrical signals;

analyzing the electrical signals to determine one or more characteristics of a texture of the product being produced;

generating an image of a sample texture, the image providing a three-dimensional surface topography of a non-homogeneous medium, the image having one or more known characteristics associated with the product being produced;

transferring the image to the on-line sensor;

analyzing data generated by the on-line sensor to determine one or more on-line measured characteristics of the image;

transferring the image to a laboratory sensor;

analyzing data generated by the laboratory sensor to determine one or more laboratory measured characteristics of the image; and comparing the one or more known characteristics of the image to the one or more on-line measured characteristics of the image and to the one or more laboratory measured characteristics of the image to determine which one of the laboratory sensor and the on-line sensor is more accurate, wherein the comparing comprises both qualitative and quantitative comparisons.

2. The method of claim 1, wherein generating the image of the sample texture comprises using mathematical fractals to generate a two-dimensional matrix of a disordered medium.

3. The method of claim 1, wherein generating the image of the sample texture comprises generating a two-dimensional matrix of a disordered medium from an image of a known textured surface.

4. The method of claim 1, wherein transferring the image comprises printing the image and presenting the printed image to the on-line sensor.

5. The method of claim 1, wherein transferring the image comprises etching the image onto a medium and presenting the etched medium to the on-line sensor.

6. The method of claim 1, wherein transferring the image comprises displaying the image and reflecting the displayed image onto the on-line sensor.

7. The method of claim 1, wherein transferring the image to the on-line sensor comprises the on-line sensor scanning the image using one of an x-ray beam and an electron beam.

8. The method of claim 1, wherein generating the image of the sample texture comprises generating a two-dimensional matrix of a disordered medium from one or more mathematical formulas.

9. The method of claim 1, wherein comparing the one or more known characteristics to the one or more on-line measured characteristics and to the one or more laboratory measured characteristics of the image comprises generating a mathematical formula of a cross-correlation between the one or more on-line measured characteristics and the one or more known characteristics and generating a mathematical formula of a cross-correlation between the one or more laboratory measured characteristics and the one or more known characteristics.

10. A device for determining one or more capabilities of an on-line sensor, the device comprising:

a module configured to generate an image of a sample texture, the image providing a three-dimensional surface topography of a non-homogeneous medium, the image having one or more known characteristics associated with a product being produced by a production process;

a module configured to transfer the image to the on-line sensor, the on-line sensor configured to (i) receive light that has interacted with the product being produced by the production process, (ii) convert the received light into electrical signals, and (iii) provide the electrical signals for analysis to determine one or more characteristics of a texture of the product being produced;

a module configured to analyze data generated by the on-line sensor based on the image to determine one or more on-line measured characteristics of the image;

a module configured to transfer the image to a laboratory sensor;

a module configured to analyze data generated by the laboratory sensor to determine one or more laboratory measured characteristics of the image; and a module configured to qualitatively and quantitatively compare the one or more known characteristics of the image to the one or more on-line measured characteristics of the image and to the one or more laboratory measured characteristics of the image to determine which one of the laboratory sensor and the online sensor is more accurate, the module comprising a qualitative comparator and a quantitative comparator.

11. The device of claim 10, wherein the module configured to generate the image comprises a computer configured to generate a two-dimensional matrix of a disordered medium.

12. The device of claim 10, wherein the module configured to transfer the image comprises a printer configured to print the image for presentation to the on-line sensor.

13. The device of claim 10, wherein the module configured to transfer the image comprises a display configured to display the image to the on-line sensor.

14. The device of claim 10, wherein the module configured to transfer the image comprises:

a display configured to display the image; and an optical device configured to project the displayed image directly onto the on-line sensor.

15. The device of claim 10, wherein the module configured to transfer the image to the laboratory sensor is further configured to etch the image onto a medium and present the etched medium to the on-line sensor.

16. A non-transitory machine-readable medium having instructions stored thereon for:

generating an image of a sample texture, the image providing a three-dimensional surface topography of a non-homogeneous medium, the image having one or more known characteristics associated with a product being produced by a production process;

transferring the image to an on-line sensor, the on-line sensor configured to (i) receive light that has interacted with the product being produced by the production process, (ii) convert the received light into electrical signals, and (iii) provide the electrical signals for analysis to determine one or more characteristics of a texture of the product being produced;

analyzing data generated by the on-line sensor based on the image to determine one or more on-line measured characteristics of the image;

transferring the image to a laboratory sensor;

analyzing data generated by the laboratory sensor to determine one or more laboratory measured characteristics of the image; and comparing the one or more known characteristics of the image to the one or more on-line measured characteristics of the image and to the one or more laboratory measured characteristics of the image to determine which one of the laboratory sensor and the online sensor is more accurate, wherein the comparing comprises both qualitative and quantitative comparisons.

17. The non-transitory machine-readable medium of claim 16, wherein the instructions for generating the image of the sample texture comprise instructions for generating a two-dimensional matrix of a disordered medium.

18. The non-transitory machine-readable medium of claim 16, wherein the instructions for transferring the image comprise instructions for displaying the image and for presenting the displayed image to the on-line sensor.

19. The non-transitory machine-readable medium of claim 16, further comprising instructions for:
   etching the image onto a medium; and
   presenting the etched medium to the on-line sensor.

20. The non-transitory machine-readable medium of claim 16, wherein the instructions for comparing the one or more measured characteristics to the one or more known characteristics comprise instructions for generating a mathematical formula of a cross-correlation between the one or more measured characteristics and the one or more known characteristics.

21. The method of claim 1, wherein the image has one or more properties of a typical texture of the product being produced by the production process.

* * * * *